United States Patent
Gellibert et al.

(10) Patent No.: US 7,141,591 B2
(45) Date of Patent: Nov. 28, 2006

(54) 1,2,4-OXADIAZOLE DERIVATIVES AS HPPAR ALPHA AGONISTS

(75) Inventors: Françoise Jeanne Gellibert, Les Ulis (FR); Kevin Guangcheng Liu, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 497 days.

(21) Appl. No.: 10/433,807

(22) PCT Filed: Dec. 6, 2001

(86) PCT No.: PCT/GB01/05400

§ 371 (c)(1), (2), (4) Date: Jan. 8, 2004

(87) PCT Pub. No.: WO02/46174

PCT Pub. Date: Jun. 13, 2002

(65) Prior Publication Data

US 2004/0132787 A1    Jul. 8, 2004

(30) Foreign Application Priority Data

Dec. 8, 2000  (GB) ................................. 0029974.3

(51) Int. Cl.
  *A61K 31/4245*  (2006.01)
  *C07D 271/06*   (2006.01)

(52) U.S. Cl. ..................... 514/364; 548/125; 548/131; 514/361

(58) Field of Classification Search ................ 548/125, 548/131; 514/361, 364
See application file for complete search history.

(56) References Cited

U.S. PATENT DOCUMENTS 6,306,873 B1 * 10/2001 Burns et al. ................. 514/299
6,875,780 B1 *  4/2005 Auerbach et al. ........... 514/345
6,964,983 B1 * 11/2005 Auerbach et al. ........... 514/568

FOREIGN PATENT DOCUMENTS

WO    WO/00/64876    11/2000
WO    WO/01/16120     3/2001

* cited by examiner

Primary Examiner—Golam M. M. Shameem
(74) Attorney, Agent, or Firm—Jennifer L. Fox

(57) ABSTRACT

A compound of formula (I) and pharmaceutically acceptable salts, solvates and hydrolysable esters thereof wherein: $X^1$ is O or S; $X^2$ is O or S; n is 1–3, One of Y and Z is N, and the other is O; $R^1$ and $R^2$ are independently halogen, H, $CH_3$, $OCH_3$ or $C_{1-3}$ alkyl; Each $R^3$ independently is halogen, $CF_3$, $C_{1-6}$ straight or branched alkyl; $R^4$ and $R^5$ are independently H or $C_{1-3}$ alkyl. y is 0, 1, 2, 3, 4 or 5.

15 Claims, No Drawings

1,2,4-OXADIAZOLE DERIVATIVES AS HPPAR ALPHA AGONISTS

This application is filed pursuant to 35 U.S.C. § 371 as a Unites States National Phase Application of Internation Application No. PCT/GB01/05400 filed Dec. 6, 2001, which claims priority from GB 0029974.3 filed in the United Kingdon on Dec. 8, 2000.

The present invention relates to certain novel compounds. In particular, the present invention relates to compounds that activate the alpha subtype of the human peroxisome proliferator activated receptor ("hPPAR alpha"). The present invention also relates to methods for preparing the compounds, their use in medicine, pharmaceutical compositions containing them and methods for the prevention or treatment of PPAR mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e., currently there are no drugs on the market that are useful for raising HDL-c >40%). (Bisgaier, C. L.; Pape, M. E. *Curr. Pharm. Des.* 1998, 4, 53–70).

Syndrome X (including metabolic syndrome) is loosely defined as a collection of abnormalities including hyperinsuinlernia, obesity, elevated levels of trigylcerides, uric acid, fibrinogen, small dense LDL-c particles, and plasminogen activator inhibitor 1 (PAI-1), and decreased levels of HDL-c.

NIDDM is described as insulin resistance which in turn causes anomalous glucose output and a decrease in glucose uptake by skeletal muscle. These factors eventually lead to impaired glucose tolerance (IGT) and hyperinsulinemia.

Peroxisome Proliferator Activated Receptors (PPARs) are orphan receptors belonging to the steroid/retinoid receptor superfamily of ligand-activated transcription factors. See, for example, Willson, T. M. and Wahli, W., *Curr. Opin. Chem. Biol.*, (1997), Vol. 1, pp 235–241.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, *Trends Endocrin. Met* 291–296, 4 (1993)).

Certain compounds that activate or otherwise interact with one or more of the PPARs have been implicated in the regulation of triglyceride and cholesterol levels in animal models. See, for example, U.S. Pat. No. 5,847,008 (Doebber et al.) and U.S. Pat. No. 5,859,051 (Adams et al.) and PCT publications WO 97/28149 (Leibowitz et al.) and WO99/04815 (Shimokawa et at.). PCT patent publication WO 00/08002 discloses certain novel compounds which exhibit activation, including dual agonist activity, to PPARgamma and PPARalpha. These compounds are indicated to be useful for the treatment of type 2 diabetes mellitus and other diseases mediated by PPARgamma and PPARalpha.

Fibrates are a class of drugs which may lower serum triglycerides 20–50%, lower LDL-c 10–15%, shift the LDL particle size from the more atherogenic small dense to normal dense LDL-c, and increase HDL-c 10–15%. Experimental evidence indicates that the effects of fibrates on serum lipids are mediated through activation of PPAR alpha. See, for example, B. Staels et al., *Curr. Pharm. Des.*, 1–14, 3 (1), (1997). Activation of PPAR alpha results in transcription of enzymes that increase fatty acid catabolism and decrease de-novo fatty acid synthesis in the liver resulting in decreased triglyceride synthesis and VLDL-c production/secretion. In addition, PPAR alpha activation decreases production of apoC-III. Reduction in apoC-III, an inhibitor of LPL activity, increases clearance of VLDL-c. See, for example, J. Auwerx et al., *Atherosclerosis*, (Shannon, Irel.), S29–S37, 124 (Suppl), (1996). PPAR alpha ligands may be useful for the treatment of dyslipidemia and cardiovascular disorders, see Fruchart, J. C., Duriez, P., and Staels, B., *Curr. Opin. Lipidol.* (1999), Vol 10, pp 245–257.

According to a first aspect of the invention there is provided a compound of formula (I) and pharmaceutically acceptable salts, solvates and hydrolysable esters thereof:

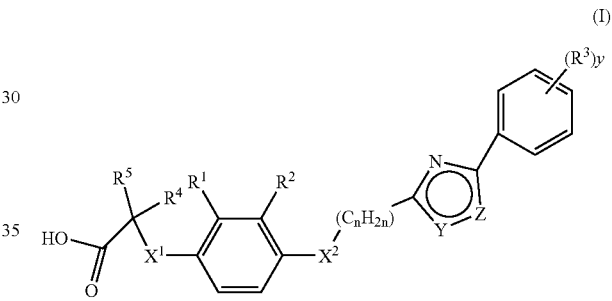

(I)

wherein:
$X^1$ is O or S;
$X^2$ is O or S;
n is 1–3;
One of Y and Z is N, and the other is O;
$R^1$ and $R^2$ are independently halogen, H, $CF_3$, $OCH_3$ or $C_{1-3}$ alkyl;
Each $R^3$ independently is halogen, $CF_3$, $C_{1-6}$ straight or branched alkyl;
$R^4$ and $R^5$ are independently H or $C_{1-3}$ alkyl.
y is 0, 1, 2, 3, 4 or 5.

In another aspect, the present invention discloses a method for prevention or treatment of a disease or condition mediated by one or more human PPAR alpha, gamma or delta ("hPPARs") comprising administration of a therapeutically effective amount of a compound of this invention. hPPAR mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, epithelial, hyperproliferative diseases including eczema and psoriasis and conditions associated with the lung or gut and regulation of appetite and food intake in subjects suffering from disorders such as obesity, anorexia bulimia, and anorexia nervosa. In particular, the compounds of this invention are useful in the treatment and prevention of diabetes and cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

In another aspect, the present invention provides a method of treatment of a patent suffering from a hPPAR mediated disease or condition comprising the administration of a therapeutically effective amount of a compound of the invention.

As used herein, "a compound of the invention" means a compound of formula (I) or a pharmaceutically acceptable salt, solvate, or hydrolyzable ester thereof.

While hydrolyzable esters are included in the scope of this invention, the acids are preferred because the data suggests that while the esters are useful compounds, it may actually be the acids to which they hydrolyze that are the active compounds. Esters that hydrolyze readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably $X^1$ is O.
Preferably $X^2$ is O.
Preferably Z is N.
Preferably n represents 1.
Preferably $R^1$ and $R^2$ independently represent H, halogen, methyl or $OCH_3$. More preferably one of $R^1$ and $R^2$ is H. In one particular preferred aspect, $R^1$ represents $CH_3$ and $R^2$ represents H. In another particular preferred aspect, both $R^1$ and $R^2$ represent H.
Preferably y is 1 and $R^3$ is preferably in the para position. Preferably $R^3$ is $C_{1-6}$ straight or branched chain alkyl or $CF_3$.
Preferably $R^4$ and $R^5$ are both $CH_3$.

While the preferred groups for each variable have generally been listed above separately for each variable, preferred compounds of this invention include those in which several or each variable in formula (I) is selected from the preferred, more preferred, or most preferred groups for each variable. Therefore, this invention is intended to include all combinations of preferred, more preferred, and most preferred groups.

The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 6.0 preferably at least 7.0 to the relevant PPAR, for example hPPARalpha in the binding assay described below, and which achieve at least 50% activation of the relevant PPAR relative to the appropriate indicated positive control in the transfection assay described below at concentrations of $10^{-5}$ M or less. More preferably, the agonists of this invention achieve 50% activation of at least one human PPAR in the relevant transfection assay at concentrations of $10^{-6}$ M or less. Preferably, the compounds of formula (I) are hPPAR agonists. More preferably the compounds are hPPARalpha agonists.

Preferred compounds of the invention include:
2-methyl-2-{4-[3-(4-tert-Butyl-phenyl)-[1,2,4]oxadiazol-5-ylmethoxy]-2-methyl-phenoxy}propionic acid ethyl ester;
2-methyl-2-{4-[3-(4-isopropyl-phenyl)-[1,2,4]oxadiazol-5-ylmethoxy]-2-methyl-phenoxy}propionic acid ethyl ester;
2-methyl-2-{4-[3-(4-trifluoromethyl-phenyl)-[1,2,4]oxadiazol-5-ylmethoxy]-2-methyl-phenoxy}-propionic acid ethyl ester;
2-methyl-2-{4-[3-(4-tert-Butyl-phenyl)-[1,2,4]oxadiazol-5-ylmethoxy]-phenoxy}-propionic acid ethyl ester;
2-methyl-2-{4-[3-(4-isopropyl-phenyl)-[1,2,4]oxadiazol-5-ylmethoxy]-phenoxy}-propionic acid ethyl ester;
2-methyl-2-{4-[3-(4-trifluoromethyl-phenyl)-[1,2,4]oxadiazol-5-ylmethoxy]-phenoxy}-propionic acid ethyl ester;
2-methyl-2-{4-[5-(4-tert-Butyl-phenyl)-[1,2,4]oxadiazol-3-ylmethoxy]-2-phenoxy}propionic acid ethyl ester;
2-methyl-2-{4-[5-(4-isopropyl-phenyl)-[1,2,4]oxadiazol-3-ylmethoxy]-phenoxy}propionic acid ethyl ester;
2-methyl-2-{4-[5-(4-trifluoromethyl-phenyl)-[1,2,4]oxadiazol-3-ylmethoxy]-phenoxy}propionic acid ethyl ester;
2-methyl-2-{4-[3-(4-tert-Butyl-phenyl)-[1,2,4]oxadiazol-5-ylmethoxy]-2-methyl-phenoxy}propionic acid;
2-methyl-2-{4-[3-(4-isopropyl-phenyl)-[1,2,4]oxadiazol-5-ylmethoxy]-2-methyl-phenoxy}propionic acid;
2-methyl-2-{4-[3-(4-trifluoromethyl-phenyl)-[1,2,4]oxadiazol-5-ylmethoxy]-2-methyl-phenoxy}-propionic acid;
2-methyl-2-{4-[3-(4-tert-Butyl-phenyl)-[1,2,4]oxadiazol-5-ylmethoxy]-phenoxy}-propionic acid;
2-methyl-2-{4-[3-(4-isopropyl-phenyl)-[1,2,4]oxadiazol-5-ylmethoxy]-phenoxy}-propionic acid;
2-methyl-2-{4-[3-(4-trifluoromethyl-phenyl)-[1,2,4]oxadiazol-5-ylmethoxy]-phenoxy}-propionic acid;
2-methyl-2-{4-[5-(4-tert-Butyl-phenyl)-[1,2,4]oxadiazol-3-ylmethoxy]-2-phenoxy}propionic acid;
2-methyl-2-{4-[5-(4-isopropyl-phenyl)-[1,2,4]oxadiazol-3-ylmethoxy]-phenoxy}propionic acid;
2-methyl-2-{4-[5-(4-trifluoromethyl-phenyl)-[1,2,4]oxadiazol-3-ylmethoxy]-phenoxy}propionic acid;
2-[4-({5-[3,5-bis(trifluoromethyl)phenyl]-1,2,4-oxadiazol-3-yl}methoxy)phenoxy]-2-methylpropanoic acid;
2-(4-{[5-(4-bromophenyl)-1,2,4-oxadiazol-3-yl]methoxy}phenoxy)-2-methylpropanoic acid.

The most preferred compound of the invention is:
2-methyl-2-{4-[3-(4-tert-Butyl-phenyl)-[1,2,4]oxadiazol-5-ylmethoxy]-2-methyl-phenoxy}-propionic acid and pharmaceutically acceptable salts, solvates and hydrolysable esters thereof.

Most preferably, the compounds of formula (I) are selective hPPAR alpha agonists. As used herein, a "selective hPPAR alpha agonist" is a hPPAR alpha agonist whose $EC_{50}$ for PPAR alpha is at least 10 fold lower than its $EC_{50}$ for PPAR gamma and PPAR delta. Such selective compounds may be referred to as "10-fold selective." $EC_{50}$ is defined in the transfection assay described below and is the concentration at which a compound achieves 50% of its maximum activity. Most preferred compounds are greater than 100-fold selective hPPAR alpha agonists (see Table 1).

TABLE 1

PPAR Transactivation activity for selected compounds.

| Example no. | human $\alpha EC_{50}$ µM | human $\delta EC_{50}$ µM | human $\gamma EC_{50}$ µM |
| --- | --- | --- | --- |
| 16 | 0.029 | 8.400 | 10.000 |
| 17 | 0.040 | 10.000 | 10.000 |
| 12 | 0.036 | 0.311 | 4.300 |
| 15 | 0.098 | 4.510 | 10.000 |
| 14 | 0.077 | 10.000 | 10.000 |
| 11 | 0.059 | 9.310 | 10.000 |
| 13 | 0.092 | 10.000 | 0.850 |
| 10 | 0.024 | 10.000 | 11.400 |

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvents". For example, a complex with water is known as a "hydrate". Solvates of the compound of formula (I) are within the scope of the invention. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier, which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 1–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR agonists (for example PPAR gamma agonists, including thiazolidinediones such as e.g. Pioglitazone and Rosiglitazone) or PPAR alpha/gamma agonists, or PPAR delta agonists wherein the PPAR delta agonists may be selective agonists for PPAR delta, have agonist activity at PPAR alpha or gamma (dual agonists) or activity at PPAR alpha and gamma (Pan agonists). The compounds may also be used in combination with antihypertensive agents such as calcium channel antagonists and ACE inhibitors. The invention thus provides in a further aspect the use of a combination comprising a compound of formula (I) with a further therapeutic agent in the treatment of a hPPAR mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

Compounds of this invention may be conveniently prepared by a general process wherein a moiety like (A) is coupled to a chloride (B) using a suitable non nucleophilic amine. Note that this synthesis is preferably carried out with the acid group protected by R although R may also represent H. Preferably, R is $C_{1-6}$ alkyl (straight chain or branched chain) which can be hydrolyzed off to give an acid of Formula (I), or if readily hydrolyzable, the resulting ester can be administered.

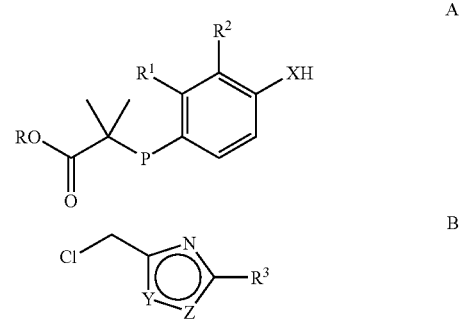

For example, when $X^1$ is O, $X^2$ is O, Y is O, Z is N, and $R^3$ is para-$CF_3$: a preferred synthesis the oxadiazoles is:

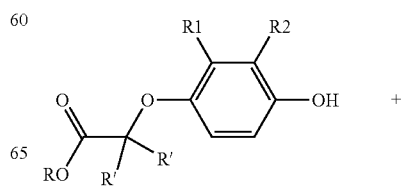

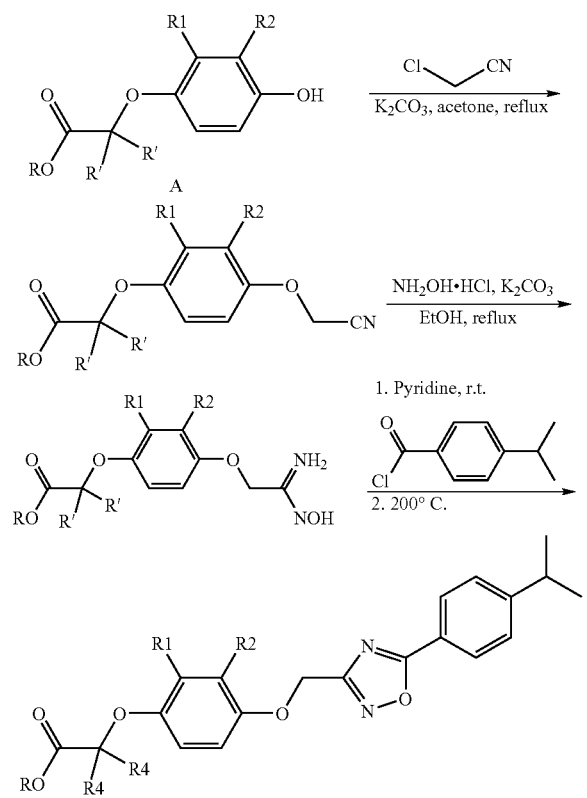

The coupling reaction between intermediate A and B may be performed in the presence of a suitable base such as potassium carbonate, cesium carbonate, in a suitable solvent such as acetonitrile or acetone preferably in the temperature range room temperature to 80° C., in a suitable solvent such as acetone or acetonitrile.

When X is O, $X^2$ is O, Y is N, Z is O, and $R^3$ is para-iPr: a preferred synthesis the oxadiazoles is:

Preferably, R is $C_{1-6}$ alkyl which can be hydrolyzed off to give an acid of Formula (I), or if readily hydrolyzable, the resulting ester can be administered.

The synthesis of intermediate of type A when X=O, $R=R^1=CH_3$, $R^2=H$ is illustrated below.

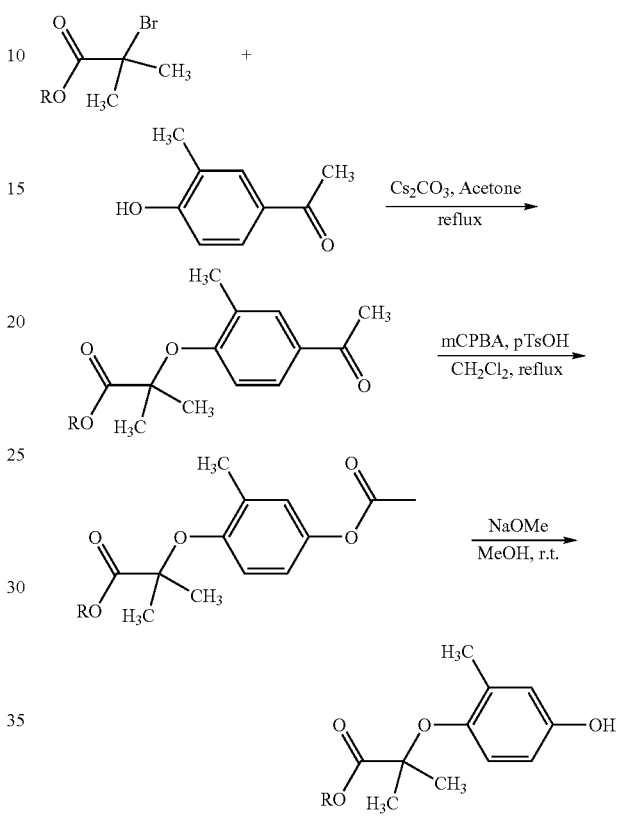

A preferred synthesis of (A) when X is O and $X^2$ is O (and $R^1=H$ and $R^2=CH_3$) is:

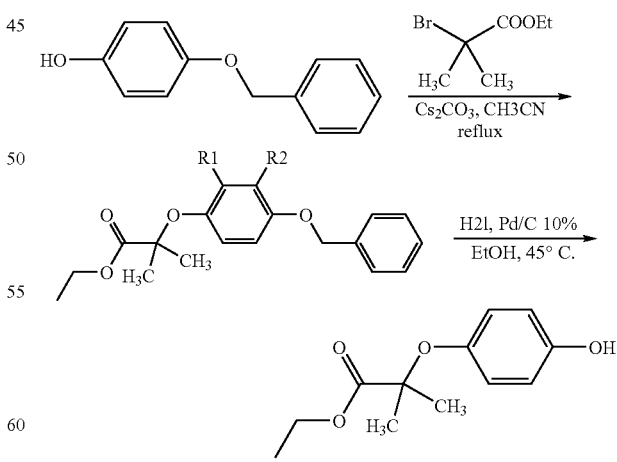

Some of the intermediates of type B are commercially available while others can be synthesized by techniques apparent to a person skilled in the art. The synthesis of intermediates of type B are illustrated below.

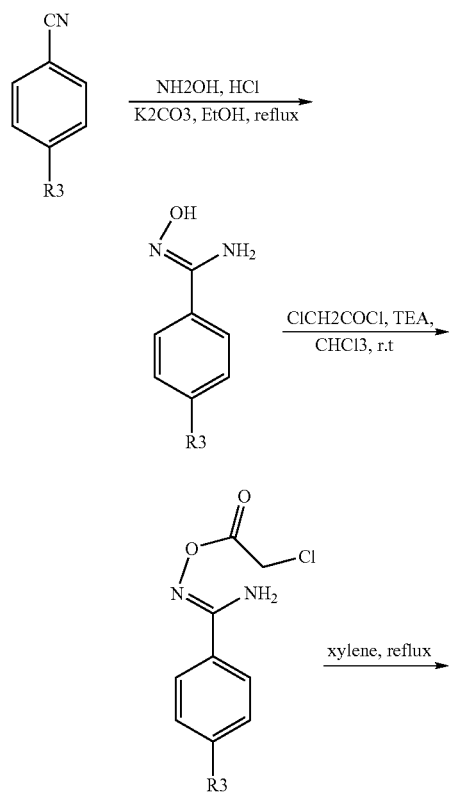

Cyclisation may be performed in a suitable solvent such as xylene or toluene at reflux.

The invention is illustrated by reference to the following Intermediates and Examples which should not be construed as limiting thereto.

The structures of the compounds were confirmed either by nuclear magnetic resonance (NMR) or mass spectrometry (MS). 1H NMR spectra were recorded on a Brucker 300 MHz spectrometer at ambient temperature. NMR shifts (δ) are given in parts per million (ppm), "mp" is melting point and is given in ° C. Column chromatography was carried out using the technique described by W. C. Still et al, J. Org. Chem. 1978, 43, 2923–2925 on Merck silica gel 60 (40–63 μM).

Compounds used as starting materials are either commercially available compounds or known compounds.

Abbreviations:

| tlc: | thin layer chromatography |
|---|---|
| DMSO-$d_6$: | deutorated dimethylsulfoxide |
| CDCl$_3$: | deutorated chloroform |
| CD$_3$OD: | deutorated methanol |
| DMF: | N,N-dimethylformamide |
| Et$_2$O: | diethylether |
| EtOAc: | Ethylacetate |
| MeOH: | Methanol |
| EtOH: | Ethanol |
| PBu3: | Tributylphosphine |
| THF: | tetrahydrofuran |
| min: | minutes |
| br: | broad |
| s: | singlet |
| d: | doublet |
| dd: | doublet of doublet |
| t: | triplet |
| q: | quartet |
| m: | multiplet |

Intermediate A1

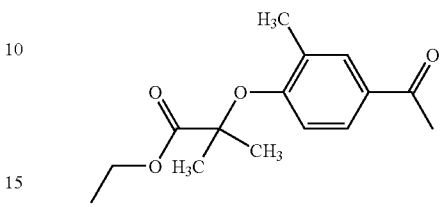

To a solution of 4'-hydroxy-3'-methylacetophenone (Acros, 25 g, 0.167 mol) in acetonitrile (300 mL) was added Cs$_2$CO$_3$ ( 2 eq, 108 g, 0.33 mol). The reaction mixture was stirred at room temperature for 30 min and then ethyl 2-bromoisobutyrate (Aldrich, 1.1 eq, 26.9 g, 0.183 mol) was added The resulting mixture was stirred at 60° C. overnight. To complete the reaction 0.5 eq of Cs$_2$CO$_3$ and 0.5 eq of Ethyl 2-bromoisobutyrate were added and the mixture was stirred 16 h at 60° C. The solvent was evaporated, the residue was solubilized in water, extracted with diethyl ether. The organic phase dried over Na$_2$SO$_4$, filtered and the solvent removed under reduced pressure to afford intermediate A1 as a brown oil (43 g, 97%). $^1$H NMR (CDCl$_3$): δ 7.87 (d, 1H), 7.77 (dd, 1H), 6.68 (d, 1H), 4.31 (q, 2H), 2.62 (s,3H), 2.35 (s, 3H), 1.74 (s, 6H), 1.30 (t, 3H).

Intermediate A2

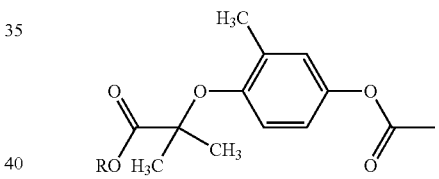

mCPBA (1.75 eq, 49.2 g, 0.285 mol) and p-TsOH (3.3 g) were added to a solution of intermediate A1 (43 g, 0.163 mol) in CH$_2$Cl$_2$. The reaction mixture was stirred under reflux for 24 h. Reaction was quenched with water and extracted with CH$_2$Cl$_2$. The organic phase was washed with NaOH 0.5M, brine and dried over Na$_2$SO$_4$. After filtration, the solvent was removed under reduced pressure to afford intermediate A2 as an orange oil (36 g, 78.9%). $^1$H NMR (CDCl$_3$): δ 6.80 (d, 1H), 6.69 (dd, 1H), 6.58 (d, 1H), 4.17 (q, 2H), 2.19 (s, 3H), 2.15 (s,3H), 1.51 (s, 6H), 1.18 (t, 3H).

Intermediate A3

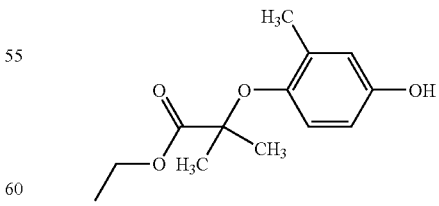

A suspension of NaOMe (1.2 eq, 8.4 g, 0.154 mmol) in MeOH (100 mL) was added to a solution of intermediate A2 ( 0.129 mol, 36 g) in MeOH (100 mL). The reaction mixture was stirred at room temperature for 30 min, then HCl N (130 mL) was added. After concentration under reduced pressure, the residue was taken off in water and extracted with CH$_2$Cl$_2$. The organic phase was dried over Na$_2$SO$_4$. After filtration, the solvent was removed under reduced pressure to afford intermediate A2 as brown solid (28 g, 91.5%). $^1$H NMR (CDCl$_3$): δ 6.55 (d, 2H), 6.53 (s, 1H), 6.43 (dd, 2H), 4.18 (q, 2H), 2.10 (s, 3H), 1.45 (s, 6H), 1.21 (t, 3H).

Intermediate A4

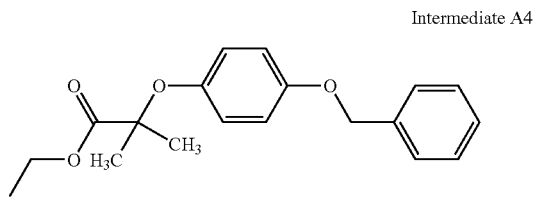

A procedure similar to that for Intermediate A1, with substitution of 4-Benzyloxyphenol (Aldrich, 0.1 mol, 20 g) for 4'-hydroxy-3'-methylacetophenone, gave the title compound as a yellow oil (29 g, 92%). $^1$H NMR (CDCl$_3$): δ 7.36–7.24 (m, 5H), 6.77 (s, 4H), 4.92 (s, 1H), 4.16 (q, 2H), 1.46 (s, 6H), 1.20 (t, 3H).

Intermediate A5

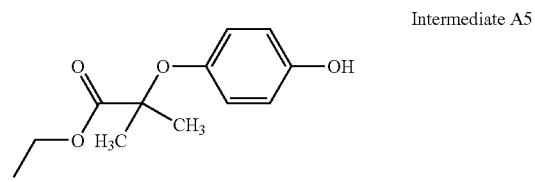

A solution of intermediate A4 (29 g, 92 mmol) in EtOH (400 mL) was hydrogenated at 45° C., in the presence of Pd/C 10% (2 g). After 3 h, the mixture was filtered through celite, washed with additional EtOH and evaporated to afford the title compound as an oil which crystallizes (20 g, 96%) $^1$H NMR (CDCl$_3$): δ 6.80 (d, 2H), 6.70 (d, 2H), 5.31 (bs, 1H), 4.26 (q, 2H), 1.54 (s, 6H), 1.29 (t, 3H).

Intermediate B1

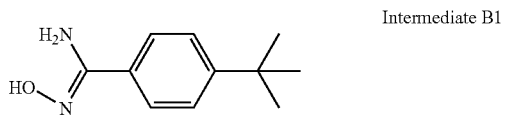

To a solution of 4-tert-Butylbenzonitrile (8.8 g, 55.3 mmol) in ethanol (300 mL) was added hydroxylamine hydrochloride (5.77 g, 83 mmol) and K$_2$CO$_3$ (15.27 g, 110 mmol). The reaction mixture was refluxed for 18 h. The mixture was filtered and the solvent was then evaporated under reduced pressure. The reaction was then partitioned between brine (150 mL) and CH$_2$Cl$_2$ (150 mL). The organic phase was further washed with brine (2×150 mL), dried over Na$_2$SO$_4$, filtered and evaporated to afford the title compound as a white solid (10.6 g, 99.7%). m.p=137–139° C.

Intermediate B2

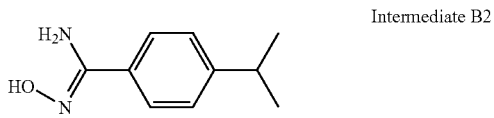

By following the method of intermediate B1 and substituting of 4-isopropyl benzonitrile (5 g, 34.4 mmol) for 4-tert-Butylbenzonitrile, intermediate B2 was obtained as an oil (3.71 g, 62%).

Intermediate B3

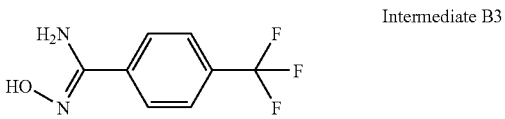

By following the method of intermediate B1 and substituting of 4-trifluoromethylbenzonitrile (25 g, 146 mmol) for 4-tert-butylbenzonitrile intermediate B3 was obtained as a pale green solid (26.9, 90.3%). m.p: 119° C.

Intermediate B4

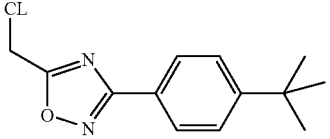

To a solution of intermediate B1 (4.7 g, 24.5 mmol) in CHCl$_3$ (40 mL) was added dropwise a solution of chloroacetyl chloride (2.32 mL, 29.37 mmol) in CHCl$_3$ (5 mL) at 0° C. After completion of the addition the temperature was raised to room temperature and then triethylamine (2.96 g, 29.37 mmol) was added. The mixture was stirred overnight at room temperature. The solvent was removed in vacuo to furnish the desired chloroacetyl derivative which was sufficiently pure to be engaged into the next reaction. The residue was dissolved in toluene (30 mL) and refluxed for 1 h. The mixture was cooled, poured into water. The phases were separated and the aqueous phase was extracted with toluene. The combined organic phases were dried over Na$_2$SO$_4$, filtered and evaporated. The crude oil was purified by flash chromatography on silica gel (CH$_2$Cl$_2$). Crystallization from hexane gave the title compound as a semi-solid (3 g, 49%).

Intermediate B5

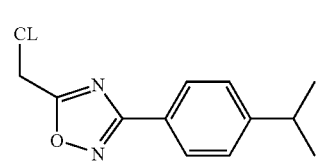

To a solution of intermediate B2 (1.85 g, 10.1 mmol) in CHCl$_3$ (50 mL) was added dropwise chloroacetyl chloride (0.85 mL, 10.6 mmol) at 0° C. After completion of the addition the temperature was raised to room temperature and then triethylamine (1.77 mL, 12.7 mmol) was added. The mixture was stirred overnight at room temperature. The mixture was diluted with CH$_2$Cl$_2$ and washed with water. The organic phase was dried over sodium sulfate, filtered and evaporated. The crude solid obtained was dissolved in xylene (50 mL) and the solution refluxed overnight. The solvent was evaporated in vacuo and the residue was purified by flash chromatography on silica gel (CH$_2$Cl$_2$). Crystallization from hexane gave the compound as off-white crystals (1.5 g, 59%). $^1$H NMR (CDCl$_3$): δ 7.94 (d, 2H), 7.28 (d, 2H), 4.67 (s, 2H), 2.90 (m, 1H), 1.22 (s, 3H), 1.20 (s, 3H). GC-MS PM: 236.

Intermediate B6

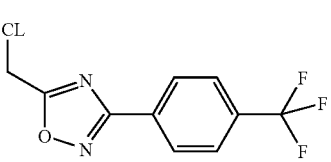

By following the method of intermediate B5 and substituting of intermediate B3 (3 g, 14.69 mmol) for intermediate B2, the title compound was obtained as a pale yellow liquid (2.44 g, 81.6%). $^1$H NMR (CDCl$_3$): δ 7.99 (d, 2H), 7.54 (d, 2H), 4.55 (s, 2H).

MS m/z: 262

Intermediate B7

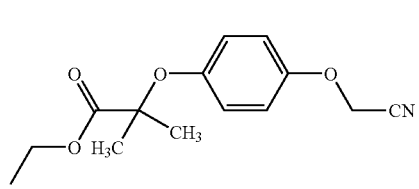

To a solution of intermediate A5 (11.3 g, 50.4 mmol) in acetonitrile (250 mL) was added chloroacetonitrile (2 eq, 6.4 mL, 0.1 mol) and Cs$_2$CO$_3$ (2 eq, 32.8 g, 0.1 mol). The reaction mixture was heated at 40° C. 1 h then refluxed for 2 h. After filtration, the solvent was removed under reduced pressure. The residue was purified by flash chromatography on silica gel (cyclohexane/EtOAc 70:30). to give the compound as a yellow oil (10 g, 75%). $^1$H NMR (CDCl$_3$): δ 6.89 (s, 4H), 4.73 (s, 2H), 4.25 (q, 2H),1.57 (s, 6H), 1.29 (t, 3H).

Intermediate B8

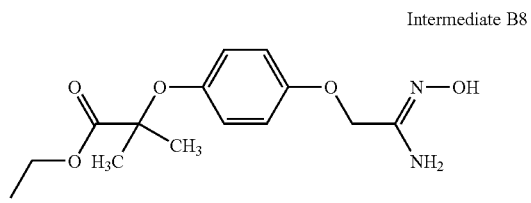

Sodium methylate (1.3 eq, 2.68 g, 49.4 mmol) was added to a solution of hydroxylamine monochloride (1.3 eq, 3.43 g, 49.4 mmol) in MeOH (80 mL). The resulting solution was stirred at room temperature for 30 min, then intermediate B7 (1 eq, 10 g, 38 mmol) was added dropwise. The mixture was reacted at room temperature overnight. After concentration under vaccuum, the residue was dissolved in CH$_2$Cl$_2$ and washed with water. The organic phase was separated and dried over Na$_2$SO$_4$, filtered and evaporated. Purification by chromatography on silica gel (cyclohexane/EtOAc 90:10) gave the title compound as an oil (7 g, 62%).

Intermediate B9

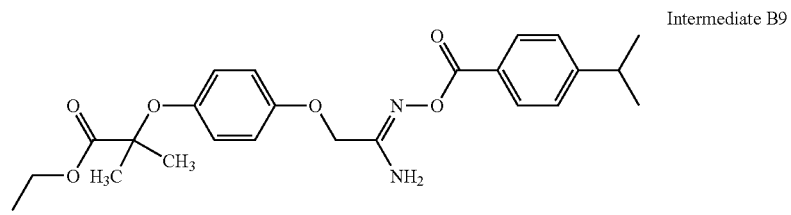

To a solution of intermediate B8 (1 eq, 0.5 g, 1.7 mmol) in pyridine(20 mL) was added p-isopropylbenzyl chloride (1.2 eq, 0.33 g, 2.02 mmol). The reaction was stirred at room temperature for 1 h. The solvent was evaporated under reduced pressure, and the residue dissolved with CH$_2$Cl$_2$. The combined organic layer was washed with H$_2$O, dried over Na$_2$SO$_4$, filtered and evaporated to dryness to give the title compound as an oil (0.29 g, 30%). $^1$H NMR (CDCl$_3$): δ 7.92 (d, 2H), 7.25 (d, 2H), 6.83–6.76 (m, 4H), 5.24 (s, 2H), 4.18 (q, 2H), 2.96–2.91 (m, 1H), 1.48 (s, 6H), 1.22 (s, 3H), 1.21 (t, 3H), 1.20 (s, 3H).

EXAMPLE 1

2-methyl-2-[4-(3-(4-tert-Butyl-phenyl)-[1,2,4]oxadiazol-5-ylmethoxy]-2-methyl-phenoxy]-propionic acid, ethyl ester To a solution of intermediate A3 (238 mg, 1 mmol) in acetone (20 mL) was added K$_2$CO$_3$ (405 mg, 3 mmol) and intermediate B4 (250 mg, 1 mmol). The resulting mixture was refluxed for 4 h. The mixture was filtered, concentrated and the residue obtained was poured into water. The aqueous phase was extracted with CH$_2$Cl$_2$, after separation the organic phase was dried over Na$_2$SO$_4$ and evaporated. The crude oil was purified by flash chromatography on silica gel (Petroleum ether/ethyl acetate 90:10) to give the title product as an oil (190 mg, 42%)

MS: m/z 453 (M+1)

EXAMPLE 2

2-methyl-2-[4-(3-(4-isopropyl-phenyl)-[1,2,4]oxadiazol-5-ylmethoxy]-2-methyl-phenoxy]-propionic acid, ethyl ester An analogous procedure to Example 1 gave the title product as an oil (320 mg, 87%). $^1$H NMR (CDCl$_3$): δ 7.94 (d, 2H), 7.26 (d, 2H), 6.76 (d, 1H), 6.55–6.65(m, 2H), 5.18 (s, 2H), 4.16 (q, 2H), 2.88 (m, 1H), 2.14 (s, 3H), 1.46 (s, 6H), 1.21 (s, 3H), 1.19 (s, 3H), 1.18 (t, 3H).

EXAMPLE 3

2-methyl-2-[4-(3-(4-trifluoromethyl-phenyl)-[1,2,4] oxadiazol-5-ylmethoxy]-2-methyl-phenoxy]-propionic acid, ethyl ester An analogous procedure to Example 1 gave the title compound as an oil which was used for next step without purification. $^1$H NMR (CDCl$_3$): δ 8.18 (d, 2H), 7.71 (d, 2H), 6.80 (d, 1H), 6.68–6.60(m, 2H), 5.24 (s, 2H), 4.20 (q, 2H), 2.18 (s, 3H), 1.50 (s, 6H), 1.22 (t, 3H).

EXAMPLE 4

2-methyl-2-[4-(3-(4-tert-Butyl-phenyl)-[1,2,4]oxadiazol-5-ylmethoxy]-phenoxy]-propionic acid, ethyl ester An analogous procedure to Example 1 gave the title compound as a white solid (48%). m.p=79–81° C. $^1$H NMR (CDCl$_3$): δ 7.95 (d, 2H), 7.44 (d, 2H), 6.87–6.76(m, 4H), 4.16 (q,2H), 5.22 (s, 2H), 1.50 (s, 9H), 1.29 (s, 6H), 1.19 (t, 3H).

EXAMPLE 5

2-methyl-2-[4-(3-(4-isopropyl-phenyl)-[1,2,4]oxa-diazol-5-ylmethoxy]-phenoxy]-propionic acid, ethyl ester An analogous procedure to Example 1 gave the title product as white crystals (74%). $^1$H NMR (CDCl$_3$): δ 8.02 (d, 2H), 7.35 (d, 2H), 6.94–6.84(m, 4H), 5.30 (s, 2H), 4.23 (q, 2H), 2.98 (m, 1H), 1.56 (s, 6H), 1.31 (s, 3H), 1.28 (s, 3H), 1.27 (t, 3H).

EXAMPLE 6

2-methyl-2-[4-(3-(4-trifluoromethyl-phenyl)-[1,2,4]oxadiazol-5-ylmethoxy]-phenoxy]propionic acid, ethyl ester An analogous procedure to Example 1 gave the title product an oil (63%). $^1$H NMR (CDCl$_3$): δ 8.16 (d, 2H), 7.68 (d, 2H), 6.86–6.77(m, 4H), 5.23 (s, 2H), 4.15 (q, 2H), 1.47 (s, 6H), 1.18 (t, 3H).

EXAMPLE 7

2-methyl-2-{4-[5-(4-isopropyl-phenyl)-[1,2,4]oxa-diazol-3-ylmethoxy]-phenoxy}propionic acid ethyl ester Intermediate B9 (0.29 g, 0.66 mmol) was heated at 200° C. for 3 min. The crude product was chromatographed on silica gel (cyclohexane/EtOAc 90:10 then 80:20) to give the title compound as a clear oil (0.17 g, 60%). $^1$H NMR (CDCl$_3$): δ 8.10 (d, 2H), 7.32 (d, 2H), 6.86 (d, 2 H), 6.78 (d,2H), 5.11 (s, 2H), 4.16 (q, 2H), 2.97–2.87 (m, 1H), 1.47 (s, 6H), 1.23 (s, 3H), 1.21 (s, 3H), 1.19 (t, 3H).

EXAMPLE 8

2-methyl-2-{4-[5-(4-tert-butyl-phenyl)-[1,2,4]oxa-diazol-3-ylmethoxy]-phenoxy}propionic acid ethyl ester By following the method of example 7 and substituting p-tert-butylbenzyl chloride for p-isopropylbenzyl chloride the title compound was obtained as a clear oil (55%). $^1$H NMR (CDCl$_3$): δ 8.02 (d, 2H), 7.48 (d, 2H), 6.87 (d,2H), 6.77 (d,2H), 5.12 (s, 2H), 4.17 (q, 2H), 1.48 (s, 6H), 1.30 (s, 9H), 1.20 (t, 3H).

EXAMPLE 9

2-methyl-2-{4-[5-(4-trifluoromethyl-phenyl)-[1,2,4]oxadiazol-3-ylmethoxy]-phenoxy}propionic acid ethyl ester By following the method of example 7 and substituting p-trifluoromethylbenzyl chloride for p-isopropylbenzyl chloride the title compound was obtained as a yellowish oil (32%). $^1$H NMR (CDCl$_3$): δ 8.27 (d, 2H), 7.79 (d, 2H), 6.93 (d, 2H), 6.91 (d, 2H), 5.19 (s, 2H), 4.21 (q, 2H), 1.52 (s, 6H), 1.25 (t, 3H).

General Procedure 1 for the Hydrolysis of the Ethyl Esters

To a solution of the ethyl ester (1 mmol) in MeOH (50 mL) was added (3 equiv.) NaOH or LiOH (1N) and the mixture heated to 60° C. overnight. The reaction is cooled to room temperature and the solution acidified with HCl (1N) and extracted with CH$_2$Cl$_2$ (3×25mL). The combined organic layers washed with H$_2$O, dried over Na$_2$SO$_4$, filtered and evaporated to dryness. The solid was titrated with Et$_2$O, collected and dried under vacuum to afford the final product.

EXAMPLE 10

2-methyl-2-[4-(3-(4-tert-butyl-phenyl)-[1,2,4]oxa-diazol-5-ylmethoxy]-2-methyl-phenoxy]-propionic acid Example 1 was reacted as described in general procedure 1 to afford the title compound as an off-white solid after recrystalization from diisopropyl ether (99% ) m.p=155–157° C.

MS: m/z 425 (M−1)

EXAMPLE 11

2-methyl-2-[4-(3-(4-isopropyl-[1,2,4]oxadiazol-5-ylmethoxy]-2-methyl-phenoxy]-propionic acid Example 2 was reacted as described in general procedure 1 to afford the title compound as white crystals after recrystalization from methanol (53%) m.p=138° C.

MS: m/z 409 (M−1)

EXAMPLE 12

2-methyl-2-{4-[3-(4-trifluoromethyl-phenyl)-[1,2,4]oxadiazol-5-ylmethoxy]-2-methyl-phenoxy}-propionic acid Example 3 was reacted as described in general procedure 1 to afford the title compound as white crystals after recrystalization from methanol (170 mg, 46%). m.p=170° C.

MS: m/z 435 (M−1)

EXAMPLE 13

2-methyl-2-[4-(3-(4-tert-butyl-phenyl)-[1,2,4]oxa-diazol-5-ylmethoxy]-phenoxy]-propionic acid Example 4 was reacted as described in general procedure 1 to afford the title compound as white crystals after recrystalization from diisopropyl ether (81%). m.p=138–140° C.

MS: m/z 409 (M−1)

EXAMPLE 14

2-methyl-2-[4-(3-(4-isopropyl-[1,2,4]oxadiazol-5-ylmethoxy]-phenoxy]-propionic acid Example 5 was reacted as described in general procedure 1 to afford the title compound as white crystals after recrystalization from diisopropyl ether (69%). m.p: 117° C.

MS: m/z 395(M−1)

EXAMPLE 15

2-methyl-2-{4-[3-(4-trifluoromethyl-phenyl)-[1,2,4] oxadiazol-5-ylmethoxy]-phenoxy}-propionic acid Example 6 was reacted as described in general procedure 1 to afford the title compound as a white solid (74%).m.p: 164° C.
MS: m/z 421(M−1)

EXAMPLE 16

2-methyl-2-{4-[5-(4-isopropyl-phenyl)-[1,2,4]oxadiazol-3-ylmethoxy]-phenoxy}propionic acid Example 7 was reacted as described in general procedure 1 to afford the title compound as a white solid (63%).m.p: 103° C. $^1$H NMR (DMSO-$d_6$): δ 7.80 (d, 2H), 7.27 (d, 2H), 6.75 (d,2H), 6.64 (d,2H), 5.02 (s, 2H), 2.81–2.76 (m, 1H), 1.22 (s, 6H), 1.04 (s, 3H), 1.02 (s, 3H).

EXAMPLE 17

2-methyl-2-{4-[5-(4-tert-butyl-phenyl)-[1,2,4]oxadiazol-3-ylmethoxy]-phenoxy}propionic acid Example 8 was reacted as described in general procedure 1 to afford the title compound as a white powder (80%).m.p: 143° C. $^1$H NMR (DMSO-$d_6$): δ 7.83 (d, 2H), 7.44 (d, 2H), 6.76 (d,2H), 6.61 (d,2H), 5.05 (s, 2H), 1.22 (s, 6H), 1.10 (s, 9H).

EXAMPLE 18

2-methyl-2-{4-[5-(4-isopropyl-phenyl)-[1,2,4]oxadiazol-3-ylmethoxy]-phenoxy}propionic acid Example 9 was reacted as described in general procedure 1 to afford the title compound as white powder. $^1$H NMR (CD$_3$OD): d 8.34 (d, 2 H, J=8.2), 7.91 (d, 2H, J=8.4), 6.96 (d, 2H, J=2.4), 6.90 (d, 2H, J=2.2), 5.23 (s, 2H), 1.49 (s, 6H).
MS: m/z 423 (M+1).

EXAMPLE 19

2-[4-({5-[3,5-bis(trifluoromethyl)phenyl]-1,2,4-oxadiazol-3-yl}methoxy)phenoxy]-2-methylpropanoic acid Starting from Intermediate B8 and 3,5-bis(trifluoromethyl)benzoyl chloride the title compound was prepared by acylation and cyclisation procedures analogous to those described for the previous examples (Intermediate B9 and Example 7). The resultant ester was hydrolysed to form the title compound. $^1$H NMR (CD$_3$OD): δ 1.48(m, 6H),3.27 (CD$_3$OH),4.86(s, 2H),5.29(s, 1H),6.81(m, 4H),8.33(m,H), 8.75(m, 2H).

EXAMPLE 20

2-(4-{[5-(4-bromophenyl)-1,2,4-oxadiazol-3-yl] methoxy}phenoxy)-2-methylpropanoic acid Starting from Intermediate B8 and 4-bromobenzoyl chloride, the title compound was prepared by acylation and cyclisation procedures analogous to those described for the previous examples (Intermediate B9 and Example 7). The resultant ester was hydrolysed to form the title compound.
$^1$H NMR (CD$_3$OD): δ1.48(s, 6H),4.85(s, 2H),6.89(m, 2H), 6.96(m, 2H),7.75(m, 2H),8.06(m, 2H).

The following intermediates and ligands were prepared for the binding and transfection assays described below:

(i) 2-{2-methyl-4-[({4-methyl-2-[4-(trifluoromethyl) phenyl]-1,3-thiazol-5-yl}methyl)sulfanyl] phenoxy}acetic acid This compound was used as a PPARdelta reference in the transfection assays described below and was prepared according to the method reported in WO200100603-A1.

(ii) 2-methyl-2-[4-{[(4-methyl-2-[4-trifluoromethylphenyl]-thiazol-5-ylcarbonyl)amino]methyl}-phenoxy]propionic acid This compound was used as a PPAR alpha reference in the transfection assay described below and was prepared according to method reported in WO200140207-A1.

(iii) 5-{4-[2-(Methyl-pyridin-2-yl-amino)-ethoxy]-benzyl}-thiazolidine-2,4-dione This compound (also referred to as rosiglitazone) was used as a PPAR gamma reference in the transfection assay described below and was prepared according to method reported in *J. Med. Chem.* 1994, 37(23), 3977.

Binding Assay:

Compounds were tested for their ability to bind to hPPAR gamma hPPAR alpha, or PPAR delta using a Scintillation Proximity Assay (SPA). The PPAR ligand binding domain (LBD) was expressed in *E. coli* as polyHis tagged fusion proteins and purified. The LBD was then labeled with biotin and immobilized on streptavidin-modified scintillation proximity beads. The beads were then incubated with a constant amount of the appropriate radioligand ($^3$H-BRL 49653 for PPAR gamma, radiolabelled 2-(4-(2-(2,3-Ditritio-1-heptyl-3-(2,4-difluorophenyl)ureido)ethyl)phenoxy)-2-methylbutanoic acid for hPPAR alpha (see WO 00/08002) and labelled GW 2433 (see Brown, P. J et al . *Chem. Biol.* 1997, 4, 909–918 for the structure and synthesis of this ligand) for PPAR delta) and variable concentrations of test compound, and after equilibration the radioactivity bound to the beads was measured by a scintillation counter. The amount of nonspecific binding, as assessed by control wells containing 50 μM of the corresponding unlabeled ligand, was subtracted from each data point. For each compound tested, plots of ligand concentration vs. CPM of radioligand bound were constructed and apparent $K_1$ values were estimated from nonlinear least squares fit of the data assuming simple competitive binding. The details of this assay have been reported elsewhere (see, Blanchard, S. G. et. al. *Development of a Scintillation Proximity Assay for Peroxisome Proliferator-Activated Receptor gamma Ligand Binding Domain. Anal. Biochem.* 1998, 257, 112–119).

Transfection Assay:

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M.; Moore, L. B.; Smith-Oliver, T. A.; Wilkison, W. O.; Willson, T. M.; Kliewer, S. A., *An antidiabetic thiazolidinedione is a high affinity ligand for peroxisome proliferator-activated receptor γ (PPARγ)*, J. Biol. Chem., 1995, 270, 12953–6. The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and β-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and β-galactosidase activity. Alkaline phosphatase activity was corrected for transfection efficiency using the β-galactosidase activity as an internal standard (see, for example, Kliewer, S. A., et. al. *Cell* 83, 813–819 (1995)). Rosiglitazone (BRL 49653) was used as a positive control in the hPPAR gamma assay. The positive control in the hPPAR alpha assays was 2-methyl-2-[4-{[(4-methyl-2-[4-trifluoromethylphenyl]-thiazol-5-yl-carbonyl)amino]methyl}-phenoxy]propionic acid. The positive control for PPAR delta assays was 2-{2-methyl-4-[({4-methyl-2-{trifluoromethyl}phenyl]-1,3-thiazol-5-yl}methyl)sulfanyl]phenoxy}acetic acid.

What is claimed is:

1. A compound of formula (I) and pharmaceutically acceptable salts, solvates and hydrolysable esters thereof

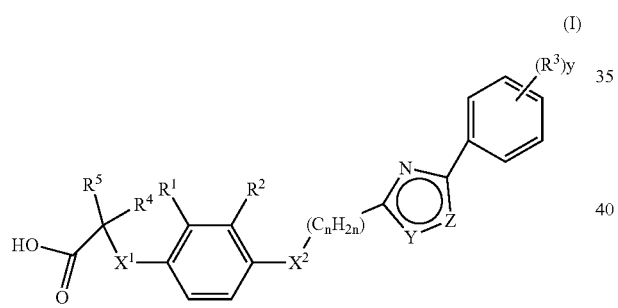

(I)

wherein:
X$^1$ is O or S;
X$^2$ is O or S;
n is 1–3;
one of Y and Z is N, and the other is O;
R$^1$ and R$^2$ are independently halogen, H, CF$_3$, OCH$_3$ or C$_{1-3}$ alkyl;
each R$^3$ independently is halogen, CF$_3$, C$_{1-6}$ straight or branched alkyl;
R$^4$ and R$^5$ are independently H or C$_{1-3}$ alkyl; and
y is 0, 1, 2, 3, 4 or 5.

2. A compound according to claim 1 wherein X$^1$ represents O.

3. A compound according to claim 1 wherein X$^2$ represents O.

4. A compound according to claim 1 wherein n represents 1.

5. A compound according to claim 1 wherein R$^1$ and R$^2$ independently represent H, halogen, methyl or OCH$_3$.

6. A compound according to claim 1 wherein R$^1$ is H or CH$_3$.

7. A compound according to claim 1 wherein R$^2$ is H.

8. A compound according to claim 1 wherein y represents 1.

9. A compound according to claim 8 wherein the R$^3$ substituent is in the para position.

10. A compound according to claim 9 wherein R$^3$ is C$_{1-6}$ straight or branched chain alkyl or CF$_3$.

11. A compound according to claim 1 wherein R$^4$ and R$^5$ are both CH$_3$.

12. A compound selected from:
2-methyl-2-{4-[3-(4-tert-Butyl-phenyl)-[1,2,4]oxadiazol-5-ylmethoxy]-2-methyl-phenoxy}propionic acid ethyl ester;
2-methyl-2-{4-[3-(4-isopropyl-phenyl)-[1,2,4]oxadiazol-5-ylmethoxy]-2-methyl-phenoxy}propionic acid ethyl ester;
2-methyl-2-{4-[3-(4-trifluoromethyl-phenyl)-[1,2,4]oxadiazol-5-ylmethoxy]-2-methyl-phenoxy}-propionic acid ethyl ester;
2-methyl-2-{4-[3-(4-tert-Butyl-phenyl)-[1,2,4]oxadiazol-5-ylmethoxy]-phenoxy}-propionic acid ethyl ester;
2-methyl-2-{4-[3-(4-isopropyl-phenyl)-[1,2,4]oxadiazol-5-ylmethoxy]-phenoxy}-propionic acid ethyl ester;
2-methyl-2-{4-[3-(4-trifluoromethyl-phenyl)-[1,2,4]oxadiazol-5-ylmethoxy]-phenoxy}-propionic acid ethyl ester;
2-methyl-2-{4-[5-(4-tert-Butyl-phenyl)-[1,2,4]oxadiazol-3-ylmethoxy]-2-phenoxy}propionic acid ethyl ester;
2-methyl-2-{4-[5-(4-isopropyl-phenyl)-[1,2,4]oxadiazol-3-ylmethoxy]-phenoxy}propionic acid ethyl ester;
2-methyl-2-{4-[5-(4-trifluoromethyl-phenyl)-[1,2,4]oxadiazol-3-ylmethoxy]-phenoxy}-propionic acid ethyl ester;
2-methyl-2-{4-[3-(4-tert-Butyl-phenyl)-[1,2,4]oxadiazol-5-ylmethoxy]-2-methyl-phenoxy}propionic acid;
2-methyl-2-{4-[3-(4-isopropyl-phenyl)-[1,2,4]oxadiazol-5-ylmethoxy]-2-methyl-phenoxy}propionic acid;
2-methyl-2-{4-[3-(4-trifluoromethyl-phenyl)-[1,2,4]oxadiazol-5-ylmethoxy]-2-methyl-phenoxy}-propionic acid;
2-methyl-2-{4-[3-(4-tert-Butyl-phenyl)-[1,2,4]oxadiazol-5-ylmethoxy]-phenoxy}-propionic acid;
2-methyl-2-{4-[3-(4-isopropyl-phenyl)-[1,2,4]oxadiazol-5-ylmethoxy]-phenoxy}-propionic acid;
2-methyl-2-{4-[3-(4-trifluoromethyl-phenyl)-[1,2,4]oxadiazol-5-ylmethoxy]-phenoxy}-propionic acid;
2-methyl-2-{4-[5-(4-tert-Butyl-phenyl)-[1,2,4]oxadiazol-3-ylmethoxy]-2-phenoxy}propionic acid;
2-methyl-2-{4-[5-(4-isopropyl-phenyl)-[1,2,4]oxadiazol-3-ylmethoxy]-phenoxy}propionic acid;
2-methyl-2-{4-[5-(4-trifluoromethyl-phenyl)-[1,2,4]oxadiazol-3-ylmethoxy]-phenoxy}propionic acid;
2-[4-({5-[3,5-bis(trifluoromethyl)phenyl]-1,2,4-oxadiazol-3-yl}methoxy)phenoxy]-2-methylpropanoic acid; and
2-(4-{[5-(4-bromophenyl)-1,2,4-oxadiazol-3-yl]methoxy}phenoxy)-2-methylpropanoic acid, and pharmaceutically acceptable salts, solvates and hydrolysable ester thereof.

13. 2-methyl-2-{4-[3-(4-tertbutyl-phenyl)-[1,2,4]oxadiazol-5-yl-methoxy]-2-methyl-phenoxy}propionic acid and pharmaceutically acceptable salts, solvates and hydrolysable esters thereof.

14. A pharmaceutical composition comprising a compound according to claim 1.

15. A pharmaceutical composition according to claim 14 further comprising a pharmaceutically acceptable diluent or carrier.

* * * * *